United States Patent [19]

Ramelot

[11] Patent Number: 4,497,214
[45] Date of Patent: Feb. 5, 1985

[54] APPARATUS FOR TAKING GASEOUS SAMPLES

[75] Inventor: Daniel L. Ramelot, Saint-Nicolas, Belgium

[73] Assignee: Centre de Recherches Metallurgiques-Centrum Voor Research in de Metallurgie, Brussels, Belgium

[21] Appl. No.: 498,410

[22] Filed: May 26, 1983

[30] Foreign Application Priority Data

May 28, 1982 [BE] Belgium .................. 6/47658

[51] Int. Cl.³ .............................................. G01N 1/24
[52] U.S. Cl. ............................. 73/863.12; 73/863.24
[58] Field of Search ........... 73/863.12, 863.23, 863.24, 73/863.31, 863.33; 55/302

[56] References Cited

U.S. PATENT DOCUMENTS

| | | | |
|---|---|---|---|
| 2,746,561 | 5/1956 | Beber et al. | 55/302 |
| 3,304,783 | 2/1967 | Quigley | 73/863.12 |
| 3,457,787 | 7/1969 | Maatsch et al. | 73/863.12 |
| 3,495,463 | 2/1970 | Howell | 73/863.24 |
| 3,517,557 | 6/1970 | Granger | 73/863.12 |
| 3,748,906 | 7/1973 | Manka | 73/863.33 |
| 3,759,087 | 9/1973 | Iwao | 73/863.12 |
| 4,090,372 | 5/1978 | Smith | 73/863.33 |

FOREIGN PATENT DOCUMENTS

| | | |
|---|---|---|
| 633848 | 4/1963 | Belgium . |
| 845879 | 7/1977 | Belgium . |
| 2127793 | 2/1972 | France . |
| 2323998 | 1/1975 | France . |

Primary Examiner—S. Clement Swisher
Attorney, Agent, or Firm—Holman & Stern

[57] ABSTRACT

The gas-sampling apparatus comprises at least two sampling probes at each sampling location and at least one sub-assembly for filtering the gas samples at each sampling location. A unit for processing and analyzing the gas samples is connected to all the sampling probes and is located as close as practicable to all the sampling locations.

12 Claims, 2 Drawing Figures

APPARATUS FOR TAKING GASEOUS SAMPLES

TECHNICAL FIELD

The present invention relates to apparatus for taking gaseous samples, particularly samples of gases containing large amounts of dust and/or moisture, such as the fumes released by oxygen converters in steelworks.

BACKGROUND ART

In known sampling devices, the high dust content of the samples gases (on average 100 $g/m^3$) causes frequent blocking of the sampling conduits and the filters.

In addition, the need to ensure a short response time has led to the installation of the devices for sampling and analysing the gases as close as possible to the sampling locations. These devices have consequently frequently been exposed to high temperatures, very dusty atmospheres, and in some cases to corrosive discharges.

These conditions are extremely detrimental, not only to the apparatus, which must be frequently serviced and unblocked, but also to the personnel carrying out these operations. Consequently, known systems only have a very limited reliability in the difficult conditions described above.

DISCLOSURE OF INVENTION

The present invention provides apparatus for taking gaseous samples, in particular from gases having a high dust and/or moisture content, which comprises:

(a) at least two sampling probes, possibly water-cooled, at each sampling location;

(b) a filtering sub-assembly located in the immediate vicinity of the sampling probes, at each sampling location;

(c) a processing and analysis unit connected to all the sampling probes and disposed with the smallest possible spacing from all the sampling locations; and, optionally, (d) a unit for recording the analysis results and for displaying abnormal and/or dangerous conditions.

In accordance with an advantageous embodiment, the filtering sub-assembly (b) comprises—for each sampling probe—an independent circuit constituted by the probe, a filter, and a pump.

In a preferred embodiment of these devices, the filter comprises a high capacity preliminary filter and a secondary filter disposed in series in the gas circuit.

It has been found advantageous, within the scope of the invention, to associate a device, which is preferably automatic, for switching the circuits so that there is always one sampling circuit in operation, even if another circuit is blocked.

If dust content of the samples is high, it is advantageous to associate with the filtering sub-assembly (b) a detector, preferably automatic, which enables the detection of any blockage taking place in the sampling circuit in operation, and in particular in the filters or in the sampling conduits. When a blockage is detected, the automatic switching device mentioned above ensures the operation of the other sampling circuit such that there is permanently a single circuit in operation per sampling location. Preferably, a further automatic device also controls the unblocking of the clogged circuit by blasting a compressed gas, for example nitrogen, preferably in the form of a series of pressure pulses of short duration, in the opposite direction in the circuit.

The three automatic devices described above are advantageously combined in a same electro-pneumatic control circuit.

The present invention also relates to a probe-filter assembly designed for the sampling and filtering of gas samples having a high dust content. In accordance with the invention, this probe-filter assembly comprises a casing to which are fitted, on the one hand, the sampling probe and, on the other hand, the filter(s).

In accordance with a preferred embodiment, the casing has the general shape of a prism of rectangular section whose bases are not perpendicular to the generatrix of the prism. Preferably, these two bases are not parallel with respect to one another and are not perpendicular to any of the lateral faces of the prism.

The filters may be mounted on the two bases of the prism, whereas the sampling probe may be mounted on one of the lateral faces. It has been found advantageous to provide the two bases with an inclination such that the filters which are fitted thereon also have a sufficient inclination to ensure the removal of the dust during a change of filter cartridge, whatever the orientation of the sampling probe in the gas conduit (from 0° to 90°).

It is also advantageous to house in the casing electrovalves ensuring the unblocking and the selection of the probes.

The casing may also advantageously be provided with means enabling an axial raking (de-clinkering) of the probe without it being necessary to dismantle the casing.

It has also been found advantageous to heat the filters, preferably by electrical methods, so as to improve the service life of the filter cartridges and to prevent water condensation.

It goes without saying that the cartridges used (material, filtration fineness) may be selected so as to ensure the best solution for each particular problem.

The various sampling assemblies are connected to a processing and analysis unit for the samples obtained which is located with the smallest practicable spacing from all the sampling locations.

In the present sampling apparatus, it is advantageous to use an analysis unit comprising infrared analysers, for example for CO and $CO_2$, a paramagnetic analyser, in particular for $O_2$, and a thermal conductivity analyser, in particular for $H_2$. These various analysers are advantageously connected to a device for correcting deviations and interference between several elements.

In addition, the recording and display unit advantageously comprises:

two continuous double curve recorders enabling the CO, $CO_2$, $O_2$, and $H_2$ analyses in particular of the gases to be made available to the operator;

a continuous recorder enabling the display of the decarburization rate, calculated for example from the CO and $CO_2$ analyses and from the measurement of the flow rate of the fumes;

a device for monitoring the hydrogen content of the fumes, with an acoustic alarm when the $H_2$ content exceeds a predetermined value, for example 6%, and/or automatic stoppage of the oxygen blasting in the converter in operation, followed by an injection of nitrogen into the fumes in the flue when the $H_2$ content exceeds a certain value, generally greater than the value mentioned above, for example 18%.

The apparatus described above may be adapted for various applications in which the continuous sampling and analysis of gas samples having a high dust content constitute an important method of monitoring the progress of a process.

The invention will now be described further, by way of example only, with reference to the accompanying drawings.

BEST MODE FOR CARRYING OUT THE INVENTION

Figure 1:
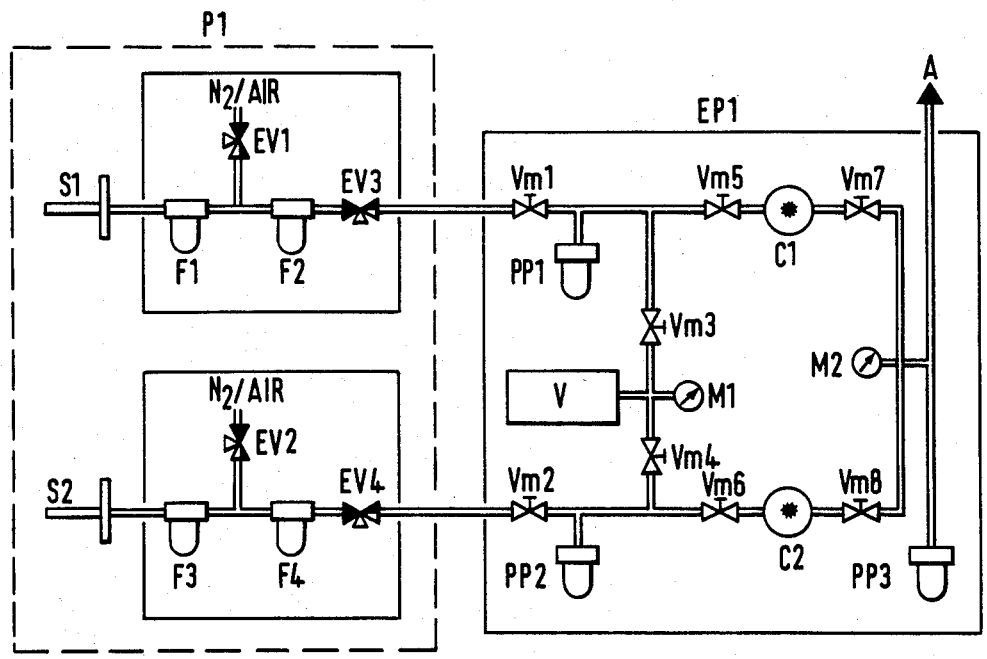
FIG. 1 diagrammatically shows, in detail, the gas circuit at a single gas sampling location.

The apparatus of FIG. 1 comprises a sampling assembly P1 and an electro-pneumatic assembly EP1 designed to detect blockages and switch probes automatically. The sampling assembly P1 comprises two probes S1 and S2, each probe being connected to a filtering and switching circuit. At any given moment, there is only one probe in operation.

The circuit of each probe S1 (S2) comprises, in this case, a preliminary filter F1 (F3) and a secondary filter F2 (F4). There is provided between these two filters, via an electro-valve EV1 (EV2), a compressed nitrogen or air supply designed to ensure the cleaning or unblocking of the probe S1 (S2) and/or the filters F1, F2 (F3, F4). The sampled gas is supplied, via an electro-valve EV3 (EV4), to the electro-pneumatic assembly EP1, and then to an analysis unit A.

When blockage of the probe in operation—S1 for example—takes place, a partial vacuum is produced in the corresponding circuit which, from a predetermined value, controls the closure of the electro-valve EV3, the opening of the electro-valve EV4 in order to bring the probe S2 into operation, and the opening of the electro-valve EV1 in order to cause the unblocking of the probe S1 or the filter F1 by the introduction, in the opposite direction, of compressed nitrogen or air. If the probe S2, provided with an identical circuit, becomes blocked in its turn, the (unblocked) probe S1 automatically becomes operational again as a result of a similar operation. The assembly EP1 also comprises pumps C1 and C2 ensuring the suction of the gases and various cleaning receptacles (PP) designed to receive possible condensates.

The operation of the sampling apparatus of the invention may be completely automatic. In this case, a probe-filter-pump assembly is automatically brought into operation when a gas release commences, for example during a refining operation carried out by oxygen blasting. If, during this operation, blockage of the said assembly is detected, for example by a vacuum control V, sampling is automatically switched to the second probe-filter-pump assembly and the first assembly is cleaned by compressed nitrogen or air in accordance with the method explained above.

At the end of blasting, the two probe-filter assemblies are both cleaned. When a further operation commences, sampling is automatically begun on the probe-filter-pump assembly which was not in operation at the end of the previous operation.

The apparatus of the invention may also be controlled manually. The selection of the probe and/or of the pump to be brought into operation is then carried out by manual valves designated Vm in FIG. 1.

As a result of the difficult conditions encountered in industrial plants, and in particular on the shopfloors of steelworks, it is particularly advantageous to house the electro-pneumatic assemblies, such as EP1, in cupboards which are sealed against dust and water spray.

Figure 2:
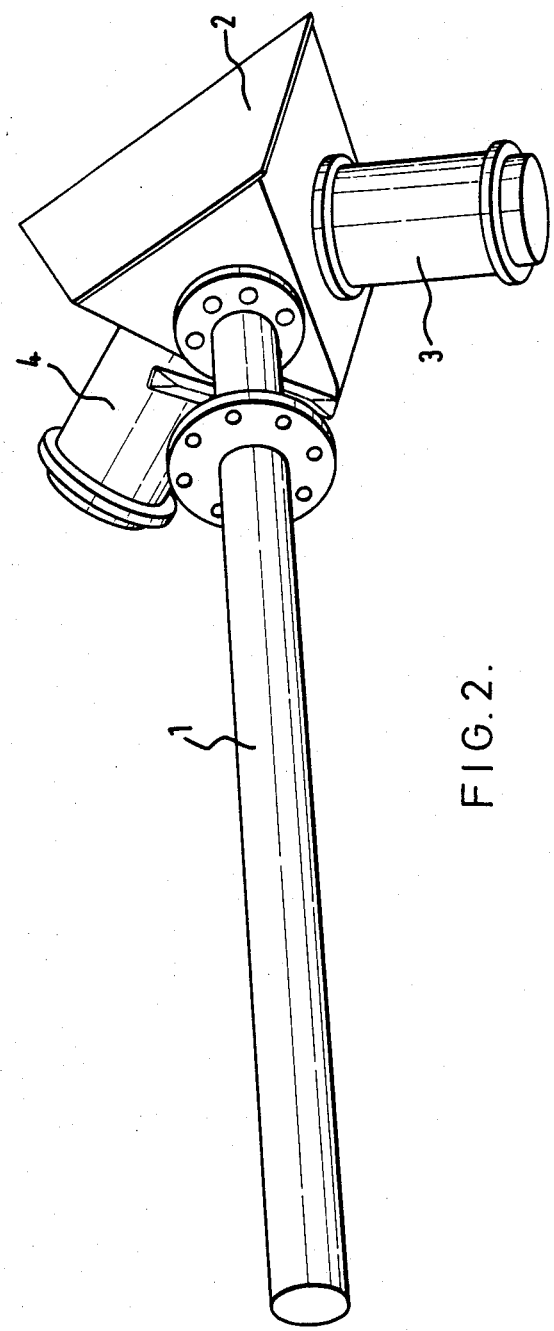
FIG. 2 shows an embodiment of a probe-filter assembly.

FIG. 2 shows an embodiment of a probe-filter assembly. This assembly is constituted by a probe 1, at the end of which there is fixed a casing 2 of prismatic shape having oblique bases. The probe is fixed to one of the lateral faces having a trapezoidal shape. The casing 2 also comprises a preliminary filter 3 and a secondary filter 4 which constitute the filter assembly. These filters are disposed in the immediate vicinity of the probe outlet so as to eliminate the risks of blockage or very long conduits.

I claim:

1. Apparatus for taking samples of gases, comprising in combination:
   (a) at least two sampling probes at each sampling location,
   (b) at least one sub-assembly for filtering the gas samples at each sampling location wherein each sub-assembly is fixed to a casing disposed at an outlet end of the sampling probe associated with said sub-assembly, said casing having a general shape of a straight prism of rectangular section whose bases are not perpendicular to the generatices of the prism, and
   (c) a unit for processing and analysing the gas samples connected to all the sampling probes and located at the smallest practicable distance form all the sampling locations.

2. The apparatus of claim 1, wherein each sampling probe is associated with a circuit comprising a sub-assembly for filtering and a pump.

3. The apparatus of claim 2, wherein the sub-assembly for filtering is disposed in the immediate vicinity of an outlet of the sampling probe with which it is associated.

4. The apparatus of claim 1, wherein each sub-assembly for filtering comprises a high capacity preliminary filter and a secondary filter disposed in series in the gas circuit.

5. The apparatus of claim 1, wherein the sub-assemblies for filtering comprise filters provided with heating means.

6. The apparatus of claim 1, further comprising means for detecting blockage of a sampling probe or filtering sub-assembly.

7. The apparatus of claim 1, further comprising means for switching the sampling probes or filtering sub-assemblies.

8. The apparatus of claim 1, further comprising means for unblocking a sampling probe or filtering sub-assembly.

9. The apparatus of claim 8, wherein the unblocking means comprises means for injecting a compressed gas in the opposite direction to the sample into the sampling probe or filtering sub-assembly.

10. The apparatus of claim 9, wherein the compressed gas is injected in the form of a series of pressure pulses of short duration.

11. The apparatus of claim 1, further comprising a unit for recording the results of analysis of the samples, connected to the processing and analysing unit.

12. Apparatus for taking samples of gases, comprising in combination:
    (a) at least two sampling probes at each sampling location;
    (b) at least one sub-assembly for filtering the gas samples at each sampling location wherein each sub-assembly is fixed to a casing disposed at an outlet end of the sampling probe associated with said sub-assembly, said sub-assembly further comprising filters mounted on two bases of the casing, said casing having general shape of a straight prism of rectangular section whose bases are not perpendicular to the generatrices of the prism and wherein the sampling probe associated with the sub-assembly is mounted on a lateral face of the casing; and (c) a unit for processing and analysing the gas samples connected to all the sampling probes and located at the smallest practicable distance from all the sampling locations.

* * * * *